US00PP36043P2

(12) United States Plant Patent
Kordes

(10) Patent No.: US PP36,043 P2
(45) Date of Patent: Jul. 30, 2024

(54) FLORIBUNDA ROSE PLANT NAMED 'KORvibaex'

(50) Latin Name: *Rosa hybrida*
Varietal Denomination: KORvibaex

(71) Applicant: W. KORDES' SÖHNE Rosenschulen GmbH & Co KG, Klein Offenseth-Sparrieshoop (DE)

(72) Inventor: Wilhelm Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 18/397,200

(22) Filed: Dec. 27, 2023

(51) Int. Cl.
*A01H 5/02* (2018.01)
*A01H 6/74* (2018.01)

(52) U.S. Cl.
USPC ..... Plt./141

(58) Field of Classification Search
USPC ..... Plt./101, 141
See application file for complete search history.

(56) References Cited

U.S. PATENT DOCUMENTS

PP14,731 P3 4/2004 Twomey et al.
PP32,109 P2 * 8/2020 Carruth ..... A01H 5/02 Plt./143
PP34,043 P2 3/2022 Kordes

* cited by examiner

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

A new and distinct variety of Floribunda rose plant, referred to by its cultivar name, 'KORvibaex', is described. The new variety forms in abundance on a substantially continuous basis attractive, yellow-orange-red colored blossoms. The vegetation is vigorous, and the growth habit is very bushy and upright. Attractive glossy, dark green foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORvibaex'.

BACKGROUND OF THE INVENTION

The new variety of Floribunda rose plant of the present invention was created by controlled breeding in May 2008 in Sparrieshoop, Germany by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) of the new variety was the 'BAlpeace' variety (U.S. Plant Pat. No. 14,731).

The parentage of the new variety can be summarized as follows:

Unnamed breeder seedling x 'BAlpeace'

The seeds resulting from the above pollination were sown and small plants were obtained which were physically and biologically different from each other. Selective study resulted in the identification of a single plant of the new variety.

The new variety has been found to undergo asexual propagation at Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of Floribunda rose plant of the present invention possesses the following combination of characteristics:

(a) forms attractive, yellow-orange-red colored blossoms,
(b) exhibits a very bushy and upright growth habit, and
(c) provides glossy, dark green foliage.

The new variety well meets the needs of the horticultural industry. It can be grown to advantage as attractive ornamentation in parks, gardens, public areas, and residential landscapes. Accordingly, it is particularly well suited for growing in the landscape.

The new variety can be readily distinguished from its ancestors. More specifically, the unnamed breeder seedling parent (i.e., the seed parent) displays a less upright growth habit and exhibits flowers with less petals. Additionally, the new variety exhibits flowers with less petals and provides a more cupped flower form compared to the flowers of the 'BAlpeace' variety (i.e., the pollen parent). Moreover, the new variety can be readily distinguished from non-parental related similar varieties. For example, the 'KORhesanwes' variety (U.S. Plant Pat. No. 34,043) displays a less upright growth habit and exhibits slightly smaller flowers with less petals.

The new variety has been named the 'KORvibaex' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a field on its own roots in Arroyo Grande, California, U.S.A. in June 2022.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a two-year-old specimen of the new variety, observed during June, while growing on its own roots in a three-gallon container in a nursery in Cochranville, Pennsylvania.

Botanical classification: *Rosa hybrida* cultivar 'KORvibaex'.

Commercial classification: Floribunda Rose.

Plant:

*Habit*.—Bushy and upright.

*Height*.—Up to 50.0 cm from the top of the soil plane.

*Width*.—Up to 48.0 cm.

Branches:

*Stem color*.—Old wood is commonly Yellow-Green Group 146B; young stems are commonly Greyed-Orange Group 166A.

*Length*.—Main stems: approximately 47.0 cm on average. — secondary stems: approximately 38.0 cm on average.

*Diameter*.—Main stems: approximately 8.0 mm on average. — secondary stems: approximately 4.0 mm on average.

*Thorns*.—Amount: moderate, 3 to 4 per internode. — young thorns: length is approximately 3.0 mm on average; width is approximately 3.0 mm at point of attachment; and color is commonly Red-Purple Group 60A. — old thorns: length is approximately 8.0 mm on average; width is approximately 3.0 mm at point of attachment; and color is commonly Red-Purple Group 60A.

Leaflets:

*Number*.—3 and 5.

*Shape*.—Ovate; apex is acute to acuminate; and base is cuneate.

*Margin*.—Serrate.

*Undulation*.—Moderate.

*Glossiness of upper side*.—Glossy.

*Texture*.—Upper surface: smooth. — under surface: smooth.

*Size*.—Terminal leaflet: length is approximately 4.0 cm on average; width is approximately 2.5 cm on average. — lower leaflets: length is approximately 3.5 to 3.75 cm on average; width is approximately 2.8 cm on average. — 5-Leaflet leaf. length is approximately 9.5 cm on average; width is approximately 7.5 cm on average.

Foliage:

*Young foliage*.—Upper surface color: commonly Green Group NN137A with venation of Red-Purple Group 59A. — under surface color: commonly Greyed-Purple Group 187C with indistinguishable venation.

*Old foliage*.—Upper surface color: commonly Green Group 139A with indistinguishable venation. — under surface color: commonly Green Group N138B with venation of Green Group 139C.

*Petiole*.—Texture: upper surface is hispidulous; under surface is smooth. — length: approximately 2.5 cm on average. — width: approximately 1.0 mm on average. — upper surface color: commonly Green Group 137A. — under surface color: commonly Green Group 137B.

*Rachis*.—Length: approximately 6.0 cm on average. — width: approximately 1.0 mm on average. — upper surface color: commonly Green Group 137A. — under surface color: commonly Green Group 137B.

*Stipules*.—Length: approximately 1.0 cm on average. — width: approximately 3.0 mm on average. — margin: entire to erose. — upper surface color: commonly Green Group 143B. — lower surface color: commonly Green Group 138A.

Inflorescence:

*Number of flowers*.—About 6 to 8 blooms on average on a plant at once.

*Number of blossoms per stem or in a cluster*.—Typically 1 bloom per stem on average.

*Peduncle*.—Color: commonly Red-Purple Group 59A. — diameter: approximately 3.0 mm on average. — length: approximately 3.0 cm on average. — surface texture: smooth.

*Sepals*.—Number: 5. — upper surface color and texture: commonly a mix of Yellow-Green Group N148A and Red Group 47A fading to Green Group 142C at base, covered in short pubescence. — under surface color and texture: commonly Green Group 143C, puberulent. — size: length is approximately 2.5 cm on average; width is approximately 8.0 mm on average. — margin: entire with extension on most sepals measuring 6.0 mm in length and 1.0 mm in width. — apex: acute to aristate. — base: truncate as it joins the receptacle.

*Buds*.—Shape: ovoid. — size: length is approximately 2.5 cm on average; width is approximately 1.2 cm on average. — color (when opening): commonly Yellow Group 13A and Red Group N45B.

*Flower*.—Form: double, cuplike. — profile: concave as it opens, and then outer petals are convex as the bloom ages and opens further. — diameter: approximately 7.0 cm on average. — height: approximately 5.5 cm on average. — duration: on the plant approximately 10 to 12 days. — petal color when first and fully opened: upper surface is multi-colored commonly with Yellow Group 8B, Yellow Group 9A, Red Group 45B, and Red Group N45B with no distinct basal spot; under surface is commonly Yellow Group 9B and Red Group 39A with no distinct basal spot. — petal color at end of bloom: upper surface is multi-colored commonly with Greyed-Purple Group 187C, Yellow Group 2D, and Red- Purple Group 61B with no distinct basal spot; under surface is commonly Red- Purple Group 62D, Red-Purple Group 63A, and White Group N155B with no distinct basal spot.

*Fragrance*.—Slight sweet scent.

*Petal*.—Number: 20 to 23 on average. — drop: good. — length: typically 3.5 cm to 4.5 cm. — width: typically 3.0 cm to 4.0 cm. — overall shape: broadly obovate. — margin: entire with moderate undulation. — apex shape: rounded to slightly cuspidate. — base shape: cuneate.

*Petaloids*.—Number: 5. — length: approximately 3.5 cm on average. — width: approximately 2.0 cm on average. — color: commonly Yellow Group 13B.

*Stamen*.—Number: approximately 105. — anthers: number is approximately 105; color is commonly Yellow-Orange Group 22A; length is approximately 5.0 mm on average; and shape is oval. — filaments: length is approximately 2.0 mm on average and color is commonly Yellow Group 12A.

*Pistils*.—Arrangement: separate and free. — number: approximately 62. — style: length is approximately 7.0 mm on average and color is commonly White Group 155A. — stigma: diameter is approximately 1.0 mm on average; shape is fan shaped.

*Receptacle*.—Diameter: approximately 8.0 mm on average. — depth: approximately 6.0 mm on average. — shape: urn shaped. — color: commonly Yellow-Green Group 144A. — surface texture: smooth.

*Pollen*.—Sparse, color is commonly Yellow-Orange Group 20A.

*Hips/seed*.—None observed.

Development:

*Vegetation*.—Vigorous and strong.

*Blossoming*.—Abundant and continuous from spring through frost; typically, in bloom outdoors from May to November in Southeastern Pennsylvania.

*Resistance to diseases*.—Very good resistance for powdery mildew (*Sphaerotheca pannosa*) and rust (*Phragmidium* sp.).

*Hardiness*.—Hardy to USDA Zone 5, further hardiness testing is in process.

The new 'KORvibaex' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'KORvibaex' characterized by the following combination of characteristics:

(a) forms attractive, yellow-orange-red colored blossoms, (b) exhibits a very bushy and upright growth habit, and (c) provides glossy, dark green foliage;

substantially as herein shown and described.

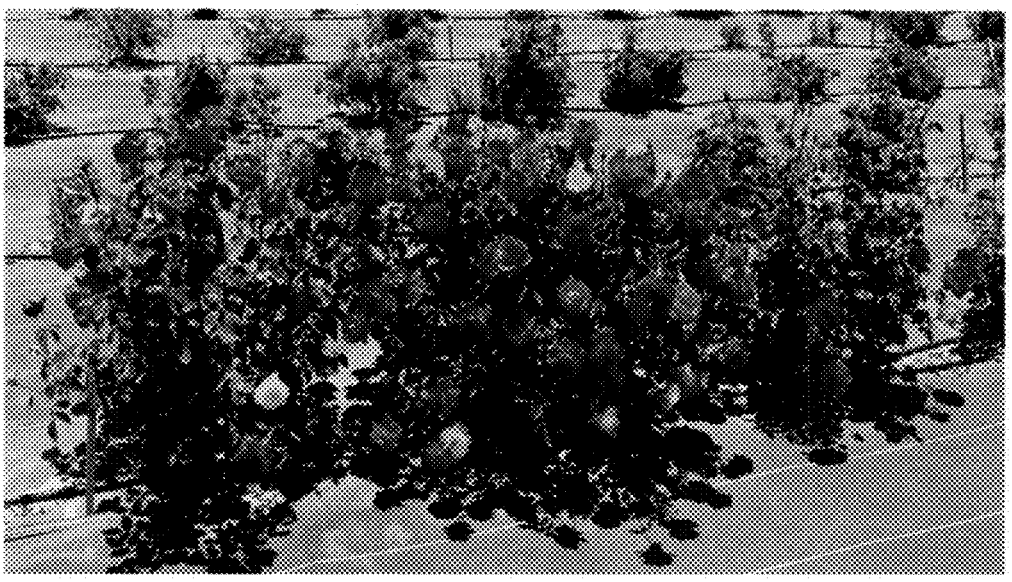

* * * * *